United States Patent
Roux

(10) Patent No.: US 10,767,165 B2
(45) Date of Patent: Sep. 8, 2020

(54) REPROGRAMMING METHOD FOR PRODUCING INDUCED PLURIPOTENT STEM CELLS (IPSC)

(71) Applicant: Centre National de la Recherche Scientifique (CNRS), Paris (FR)

(72) Inventor: Pierre Roux, Saint Gely-du Fesc (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/547,212

(22) PCT Filed: Feb. 1, 2016

(86) PCT No.: PCT/EP2016/052085
§ 371 (c)(1),
(2) Date: Jul. 28, 2017

(87) PCT Pub. No.: WO2016/120493
PCT Pub. Date: Aug. 4, 2016

(65) Prior Publication Data
US 2018/0023056 A1 Jan. 25, 2018

(30) Foreign Application Priority Data
Jan. 30, 2015 (EP) .................................... 15305145

(51) Int. Cl.
*C12N 15/00* (2006.01)
*C12N 5/00* (2006.01)
*C12N 5/074* (2010.01)

(52) U.S. Cl.
CPC ........ *C12N 5/0696* (2013.01); *C12N 2501/40* (2013.01); *C12N 2501/998* (2013.01); *C12N 2506/1307* (2013.01); *C12N 2510/00* (2013.01)

(58) Field of Classification Search
USPC .................................................. 435/325, 455
See application file for complete search history.

(56) References Cited

U.S. PATENT DOCUMENTS

| 8,530,238 | B2* | 9/2013 | Yamanaka | C12N 5/0696 |
| | | | | 435/325 |
| 8,703,413 | B2* | 4/2014 | Daley | G01N 33/5023 |
| | | | | 435/4 |
| 9,394,524 | B2* | 7/2016 | Lin | C12N 5/0696 |
| 9,404,124 | B2* | 8/2016 | Okita | C12N 5/0696 |

FOREIGN PATENT DOCUMENTS

| WO | 2011000891 A1 | 1/2011 |
| WO | 2012/044979 A2 | 4/2012 |
| WO | WO 2012/044979 | * 4/2012 |

OTHER PUBLICATIONS

Bourdon (Brit. J. Cancer, 2007, vol. 97, p. 277-282).*
Feng (Cell Stem Cell Review, 2009, vol. 4, p. 301-312).*
Bernard, H. et al., The p53 isoform, delta133p53alpha, stimulates angiogenesis and tumour progression, Oncogene, Jun. 25, 2012 (Jun. 25, 2012), vol. 32, No. 17, pp. 2150-2160.
Bourdon, Jean-Christophe et al., p53 isoforms can regulate p53 transcriptional activity, Genes and Development, Sep. 1, 2005 (Sep. 1, 2005),vol. 19, No. 18, pp. 2122-2137.
Kawamura, T. et al., Linking the p53 tumour suppressor pathway to somatic cell reprogramming, Nature, Aug. 1, 2009 (Aug. 1, 2009),vol. 460, No. 7259, pp. 1140-1145.
Khoury, M. P. , et al, p53 Isoforms: An Intracellular Microprocessor?, Genes & Cancer, Apr. 1, 2011 (Apr. 1, 2011), vol. 2, No. 4, pp. 453-465.
Takenaka, C. et al., Effective generation 8-12 of iPS cells from CD34+ cord blood cells by inhibition of p53, Experimental Hematology, Feb. 1, 2010 (Feb. 1, 2010) vol. 38, No. 2, pp. 154-162.
Aoubala et al. "p53 directly transactivates ?133p53?, regulating cell fate outcome in response to DNA damage", Cell Death Differ. Feb. 2011;18(2):248-58. doi: 10.1038/cdd.2010.91.
Baus et al. "Permanent cell cycle exit in G2 phase after DNA damage in normal human fibroblasts". The EMBO Journal 22 : 3992-4002, 2003.
Bourdon, J.C. (2007). p53 and its isoforms in cancer. Br J Cancer 97, 277-282.
Gire et al. "DNA damage checkpoint kinase Chk2 triggers replicative senescence". The EMBO Journal 23:2554-63, 2004.
Golebiewska et al. "Critical appraisal of the side population assay in stem cell and cancer stem cell research". Cell Stem Cell. Feb. 4, 2011;8(2):136-47.
Hofstetter et al. "The N-terminally truncated p53 isoform Delta40p53 influences prognosis in mucinous ovarian cancer". International Journal of Gynecological Cancer : Official Journal of the International Gynecological Cancer Society 22, 372-379. (2012).
Hong et al. "Suppression of induced pluripotent stem cell generation by the p53-p21 pathway". Nature 460, 1132-1135. (2009).
Jullien et al. "Eroded human telomeres are more prone to remain uncapped and to trigger a G2 checkpoint response". Nucleic Acids Research 41, 900-11. (2013).
Lapasset et al. "Rejuvenating senescent and centenarian human cells by reprogramming through the pluripotent state.", Genes Dev. Nov. 1, 2011;25(21):2248-53.
Li et al. (2012). Distinct regulatory mechanisms and functions for p53-activated and p53-repressed DNA damage response genes in embryonic stem cells. Mol Cell 46, 30-42.

(Continued)

Primary Examiner — Michael C Wilson
(74) *Attorney, Agent, or Firm* — Banner & Witcoff, Ltd.

(57) ABSTRACT

The present invention is in the field of stem cells. Particularly, the present invention relates to a reprogramming method for producing induced pluripotent stem cells (iPSC) by transducing somatic differentiated cells with a viral vector expressing Δ133p53β isoform, Δ133p53γ isoform or both Δ133p53β and Δ133p53γ isoforms; to induced pluripotent stem cells as produced by this method; to uses thereof in cell therapy and as an in vitro model for studying various diseases; and to a method for detecting iPSC.

13 Claims, 8 Drawing Sheets

Specification includes a Sequence Listing.

(56) References Cited

OTHER PUBLICATIONS

Lin et al. "p53 induces differentiation of mouse embryonic stem cells by suppressing Nanog expression", Nat Cell Biol. Feb. 2005;7(2):165-71.

Lin et al. "Embryoid body formation from human pluripotent stem cells in chemically defined E8 media" (Jun. 1, 2014), StemBook, ed. The Stem Cell Research Community, StemBook.

Marcel et al, 2010 "?160p53 is a novel N-terminal p53 isoform encoded by ?133p53 transcript". FEBS Letters 584 (2010)4463-4468.

Tapia et al. "p53 connects tumorigenesis and reprogramming to pluripotency", J Exp Med. Sep. 27, 2010;207(10):2045-8. doi: 10.1084/jem.20101866.

Telford WG. Stem cell side population analysis and sorting using DyeCycle violet. Curr Protoc Cytom. Jan. 2010; Chapter 9:Unit9.30.

Terrier et al. "Influenza A viruses control expression of proviral human p53 isoforms p53? and Delta133p53?". J Virol. Aug. 2012;86(16):8452-60. 10.1128/JVI.07143-11.

\* cited by examiner

SEQUENCE LISTING

```
<160> NUMBER OF SEQ ID NOS: 6

<210> SEQ ID NO 1
<211> LENGTH: 209
<212> TYPE: PRT
<213> ORGANISM: Homo sapiens
<220> FEATURE:
<221> NAME/KEY: SITE
<222> LOCATION: (1)..(209)
<223> OTHER INFORMATION: Homo sapiens tumor protein p53, isoform
      delta133p53beta (Genbank NP_001119588.1)

<400> SEQUENCE: 1

Met Phe Cys Gln Leu Ala Lys Thr Cys Pro Val Gln Leu Trp Val Asp
1               5                   10                  15

Ser Thr Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Pro Leu Asp
            180                 185                 190

Gly Glu Tyr Phe Thr Leu Gln Asp Gln Thr Ser Phe Gln Lys Glu Asn
        195                 200                 205

Cys

<210> SEQ ID NO 2
<211> LENGTH: 2404
<212> TYPE: DNA
<213> ORGANISM: Homo sapiens
<220> FEATURE:
<221> NAME/KEY: misc_feature
```

<223> OTHER INFORMATION: Homo sapiens tumor protein p53, isoform
     delta133p53beta (Genbank NM_001126116.1)

<400> SEQUENCE: 2

| | | | | | |
|---|---|---|---|---|---|
| tgaggccagg | agatggaggc | tgcagtgagc | tgtgatcaca | ccactgtgct | ccagcctgag | 60 |
| tgacagagca | agaccctatc | tcaaaaaaaa | aaaaaaaaaa | gaaaagctcc | tgaggtgtag | 120 |
| acgccaactc | tctctagctc | gctagtgggt | tgcaggaggt | gcttacgcat | gtttgtttct | 180 |
| ttgctgccgt | cttccagttg | ctttatctgt | tcacttgtgc | cctgactttc | aactctgtct | 240 |
| ccttcctctt | cctacagtac | tcccctgccc | tcaacaagat | gttttgccaa | ctggccaaga | 300 |
| cctgccctgt | gcagctgtgg | gttgattcca | cacccccgcc | cggcacccgc | gtccgcgcca | 360 |
| tggccatcta | caagcagtca | cagcacatga | cggaggttgt | gaggcgctgc | ccccaccatg | 420 |
| agcgctgctc | agatagcgat | ggtctggccc | ctcctcagca | tcttatccga | gtggaaggaa | 480 |
| atttgcgtgt | ggagtatttg | gatgacagaa | acacttttcg | acatagtgtg | gtggtgccct | 540 |
| atgagccgcc | tgaggttggc | tctgactgta | ccaccatcca | ctacaactac | atgtgtaaca | 600 |
| gttcctgcat | gggcggcatg | aaccggaggc | ccatcctcac | catcatcaca | ctggaagact | 660 |
| ccagtggtaa | tctactggga | cggaacagct | ttgaggtgcg | tgtttgtgcc | tgtcctggga | 720 |
| gagaccggcg | cacagaggaa | gagaatctcc | gcaagaaagg | ggagcctcac | cacgagctgc | 780 |
| ccccagggag | cactaagcga | gcactgccca | acaacaccag | ctcctctccc | cagccaaaga | 840 |
| agaaaccact | ggatggagaa | tatttcaccc | ttcaggacca | gaccagcttt | caaaaagaaa | 900 |
| attgttaaag | agagcatgaa | aatggttcta | tgactttgcc | tgatacagat | gctacttgac | 960 |
| ttacgatggt | gttacttcct | gataaactcg | tcgtaagttg | aaaatattat | ccgtgggcgt | 1020 |
| gagcgcttcg | agatgttccg | agagctgaat | gaggccttgg | aactcaagga | tgcccaggct | 1080 |
| gggaaggagc | aggggggag | cagggctcac | tccagccacc | tgaagtccaa | aaagggtcag | 1140 |
| tctacctccc | gccataaaaa | actcatgttc | aagacagaag | ggcctgactc | agactgacat | 1200 |
| tctccacttc | ttgttcccca | ctgacagcct | cccaccccca | tctctccctc | cctgccatt | 1260 |
| ttgggttttg | ggtctttgaa | cccttgcttg | caataggtgt | gcgtcagaag | cacccaggac | 1320 |
| ttccatttgc | tttgtcccgg | ggctccactg | aacaagttgg | cctgcactgg | tgttttgttg | 1380 |
| tggggaggag | gatggggagt | aggacatacc | agcttagatt | ttaaggtttt | tactgtgagg | 1440 |
| gatgtttggg | agatgtaaga | aatgttcttg | cagttaaggg | ttagtttaca | atcagccaca | 1500 |
| ttctaggtag | ggcccacttc | accgtactaa | ccagggaag | ctgtccctca | ctgttgaatt | 1560 |
| ttctctaact | tcaaggccca | tatctgtgaa | atgctggcat | ttgcacctac | ctcacagagt | 1620 |
| gcattgtgag | ggttaatgaa | ataatgtaca | tctggccttg | aaaccacctt | ttattacatg | 1680 |
| gggtctagaa | cttgaccccc | ttgagggtgc | ttgttccctc | tccctgttgg | tcggtgggtt | 1740 |
| ggtagtttct | acagttgggc | agctggttag | gtagagggag | ttgtcaagtc | tctgctggcc | 1800 |
| cagccaaacc | ctgtctgaca | acctcttggt | gaaccttagt | acctaaaagg | aaatctcacc | 1860 |
| ccatcccaca | ccctggagga | tttcatctct | tgtatatgat | gatctggatc | caccaagact | 1920 |
| tgttttatgc | tcagggtcaa | tttcttttt | cttttttttt | tttttttttc | ttttctttg | 1980 |
| agactgggtc | tcgctttgtt | gcccaggctg | gagtggagtg | gcgtgatctt | ggcttactgc | 2040 |
| agcctttgcc | tccccggctc | gagcagtcct | gcctcagcct | ccggagtagc | tgggaccaca | 2100 |
| ggttcatgcc | accatggcca | gccaactttt | gcatgttttg | tagagatggg | gtctcacagt | 2160 |
| gttgcccagg | ctggtctcaa | actcctgggc | tcaggcgatc | cacctgtctc | agcctcccag | 2220 |

```
agtgctggga ttacaattgt gagccaccac gtccagctgg aagggtcaac atcttttaca    2280
ttctgcaagc acatctgcat tttcacccca cccttcccct ccttctccct ttttatatcc    2340 cattttata tcgatctctt attttacaat aaaactttgc tgccacctgt gtgtctgagg    2400
ggtg                                                                 2404
```

<210> SEQ ID NO 3
<211> LENGTH: 214
<212> TYPE: PRT
<213> ORGANISM: Homo sapiens
<220> FEATURE:
<221> NAME/KEY: SITE
<222> LOCATION: (1)..(214)
<223> OTHER INFORMATION: Homo sapiens tumor protein p53, isoform
      delta133p53gamma (Genbank NP_001119589.1)

<400> SEQUENCE: 3

```
Met Phe Cys Gln Leu Ala Lys Thr Cys Pro Val Gln Leu Trp Val Asp
1               5                   10                  15

Ser Thr Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210
```

<210> SEQ ID NO 4
<211> LENGTH: 2331
<212> TYPE: DNA
<213> ORGANISM: Homo sapiens
<220> FEATURE:
<221> NAME/KEY: misc_feature
<223> OTHER INFORMATION: Homo sapiens tumor protein p53, isoform
      delta133p53gamma (Genbank NM_001126117.1)

<400> SEQUENCE: 4

```
tgaggccagg agatggaggc tgcagtgagc tgtgatcaca ccactgtgct ccagcctgag    60
tgacagagca agaccctatc tcaaaaaaaa aaaaaaaaa gaaaagctcc tgaggtgtag    120
```

```
acgccaactc tctctagctc gctagtgggt tgcaggaggt gcttacgcat gtttgtttct        180
ttgctgccgt cttccagttg ctttatctgt tcacttgtgc cctgactttc aactctgtct        240
ccttcctctt cctacagtac tcccctgccc tcaacaagat gttttgccaa ctggccaaga        300
cctgccctgt gcagctgtgg gttgattcca caccccgcc cggcacccgc gtccgcgcca         360
tggccatcta caagcagtca cagcacatga cggaggttgt gaggcgctgc ccccaccatg        420
agcgctgctc agatagcgat ggtctggccc ctcctcagca tcttatccga gtggaaggaa        480
atttgcgtgt ggagtatttg gatgacagaa acactttcg acatagtgtg gtggtgccct         540
atgagccgcc tgaggttggc tctgactgta ccaccatcca ctacaactac atgtgtaaca        600
gttcctgcat gggcggcatg aaccggaggc ccatcctcac catcatcaca ctggaagact        660
ccagtggtaa tctactggga cggaacagct tgaggtgcg tgtttgtgcc tgtcctggga         720
gagaccggcg cacagaggaa gagaatctcc gcaagaaagg ggagcctcac cacgagctgc        780
ccccagggag cactaagcga gcactgccca caacaccag ctcctctccc cagccaaaga         840
agaaaccact ggatggagaa tatttcaccc ttcagatgct acttgactta cgatggtgtt        900
acttcctgat aaactcgtcg taagttgaaa atattatccg tgggcgtgag cgcttcgaga        960
tgttccgaga gctgaatgag gccttggaac tcaaggatgc ccaggctggg aaggagccag       1020
gggggagcag ggctcactcc agccacctga gtccaaaaa gggtcagtct acctcccgcc        1080
ataaaaaact catgttcaag acagaagggc ctgactcaga ctgacattct ccacttcttg       1140
ttccccactg acagcctccc accccatct ctccctcccc tgccatttg ggttttgggt         1200
cttttgaaccc ttgcttgcaa taggtgtgcg tcagaagcac ccaggacttc catttgcttt      1260
gtcccggggc tccactgaac aagttggcct gcactggtgt tttgttgtgg ggaggaggat       1320
ggggagtagg acataccagc ttagatttta aggttttttac tgtgagggat gtttgggaga      1380
tgtaagaaat gttcttgcag ttaagggtta gtttacaatc agccacattc taggtagggg       1440
cccacttcac cgtactaacc agggaagctg tccctcactg ttgaattttc tctaacttca       1500
aggcccatat ctgtgaaatg ctggcatttg cacctacctc acagagtgca ttgtgagggt       1560
taatgaaata atgtacatct ggccttgaaa ccacctttta ttacatgggg tctagaactt       1620
gacccccttg agggtgcttg ttccctctcc ctgttggtcg gtgggttggt agtttctaca       1680
gttgggcagc tggttaggta gagggagttg tcaagtctct gctggcccag ccaaaccctg       1740
tctgacaacc tcttggtgaa ccttagtacc taaaaggaaa tctcacccca tcccacaccc       1800
tggaggattt catctcttgt atatgatgat ctggatccac caagacttgt tttatgctca       1860
gggtcaattt cttttttctt tttttttttt tttttctttt ttctttgaga ctgggtctcg       1920
ctttgttgcc caggctggag tggagtgcgc tgatcttggc ttactgcagc ctttgcctcc       1980
ccggctcgag cagtcctgcc tcagcctccg gagtagctgg gaccacaggt tcatgccacc       2040
atggccagcc aacttttgca tgttttgtag agatgggtc tcacagtgtt gcccaggctg        2100
gtctcaaaact cctgggctca ggcgatccac ctgtctcagc ctcccagagt gctgggatta     2160
caattgtgag ccaccacgtc cagctggaag ggtcaacatc ttttacattc tgcaagcaca       2220
tctgcatttt caccccaccc ttcccctcct tctcccttttt tatatcccat ttttatatcg      2280
atctcttatt ttacaataaa actttgctgc cacctgtgtg tctgagggt g                 2331
```

<210> SEQ ID NO 5
<211> LENGTH: 393
<212> TYPE: PRT
<213> ORGANISM: Homo sapiens

```
<220> FEATURE:
<221> NAME/KEY: SITE
<222> LOCATION: (1)..(393)
<223> OTHER INFORMATION: Homo sapiens tumor protein p53 (Genbank
      NP_000537.3)

<400> SEQUENCE: 5
```

| Met | Glu | Glu | Pro | Gln | Ser | Asp | Pro | Ser | Val | Glu | Pro | Pro | Leu | Ser | Gln |
|---|---|---|---|---|---|---|---|---|---|---|---|---|---|---|---|
| 1 | | | | 5 | | | | | 10 | | | | | 15 | |

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
 50                  55                  60

Arg Met Pro Glu Ala Ala Pro Pro Val Ala Pro Ala Pro Ala Ala Pro
65                   70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
             100                 105                 110

Phe Leu His Ser Gly Thr Ala Lys Ser Val Thr Cys Thr Tyr Ser Pro
         115                 120                 125

Ala Leu Asn Lys Met Phe Cys Gln Leu Ala Lys Thr Cys Pro Val Gln
130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                 165                 170                 175

Pro His His Glu Arg Cys Ser Asp Ser Asp Gly Leu Ala Pro Pro Gln
             180                 185                 190

His Leu Ile Arg Val Glu Gly Asn Leu Arg Val Glu Tyr Leu Asp Asp
         195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                 245                 250                 255

Leu Glu Asp Ser Ser Gly Asn Leu Leu Gly Arg Asn Ser Phe Glu Val
             260                 265                 270

Arg Val Cys Ala Cys Pro Gly Arg Asp Arg Arg Thr Glu Glu Glu Asn
         275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                 325                 330                 335

Arg Phe Glu Met Phe Arg Glu Leu Asn Glu Ala Leu Glu Leu Lys Asp
             340                 345                 350

Ala Gln Ala Gly Lys Glu Pro Gly Gly Ser Arg Ala His Ser Ser His
         355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 6
<211> LENGTH: 2586
<212> TYPE: DNA
<213> ORGANISM: Homo sapiens
<220> FEATURE:
<221> NAME/KEY: misc_feature
<223> OTHER INFORMATION: Homo sapiens tumor protein p53 cDNA (Genbank
      NM_000546.4)

<400> SEQUENCE: 6

| | | | | | |
|---|---|---|---|---|---|
| gattggggtt | tcccctccc | atgtgctcaa | gactggcgct | aaaagttttg | agcttctcaa | 60 |
| aagtctagag | ccaccgtcca | gggagcaggt | agctgctggg | ctccggggac | actttgcgtt | 120 |
| cgggctggga | gcgtgctttc | cacgacggtg | acacgcttcc | ctggattggc | agccagactg | 180 |
| ccttccgggt | cactgccatg | gaggagccgc | agtcagatcc | tagcgtcgag | ccccctctga | 240 |
| gtcaggaaac | attttcagac | ctatggaaac | tacttcctga | aaacaacgtt | ctgtcccct | 300 |
| tgccgtccca | agcaatggat | gatttgatgc | tgtccccgga | cgatattgaa | caatggttca | 360 |
| ctgaagaccc | aggtccagat | gaagctccca | gaatgccaga | ggctgctccc | ccgtggccc | 420 |
| ctgcaccagc | agctcctaca | ccggcggccc | ctgcaccagc | cccctcctgg | ccctgtcat | 480 |
| cttctgtccc | ttcccagaaa | acctaccagg | gcagctacgg | tttccgtctg | ggcttcttgc | 540 |
| attctgggac | agccaagtct | gtgacttgca | cgtactcccc | tgccctcaac | aagatgtttt | 600 |
| gccaactggc | caagacctgc | cctgtgcagc | tgtgggttga | ttccacaccc | ccgcccggca | 660 |
| cccgcgtccg | cgccatggcc | atctacaagc | agtcacagca | catgacggag | gttgtgaggc | 720 |
| gctgccccca | ccatgagcgc | tgctcagata | gcgatggtct | ggcccctcct | cagcatctta | 780 |
| tccgagtgga | aggaaatttg | cgtgtggagt | atttggatga | cagaaacact | tttcgacata | 840 |
| gtgtggtggt | gccctatgag | ccgcctgagg | ttggctctga | ctgtaccacc | atccactaca | 900 |
| actacatgtg | taacagttcc | tgcatgggcg | gcatgaaccg | gaggcccatc | ctcaccatca | 960 |
| tcacactgga | agactccagt | ggtaatctac | tgggacggaa | cagctttgag | gtgcgtgttt | 1020 |
| gtgcctgtcc | tgggagagac | cggcgcacag | aggaagagaa | tctccgcaag | aaaggggagc | 1080 |
| ctcaccacga | gctgccccca | gggagcacta | agcgagcact | gcccaacaac | accagctcct | 1140 |
| ctccccagcc | aaagaagaaa | ccactggatg | gagaatattt | cacccttcag | atccgtgggc | 1200 |
| gtgagcgctt | cgagatgttc | cgagagctga | atgaggcctt | ggaactcaag | gatgcccagg | 1260 |
| ctgggaagga | gccaggggggg | agcagggctc | actccagcca | cctgaagtcc | aaaaagggtc | 1320 |
| agtctacctc | ccgccataaa | aaactcatgt | tcaagacaga | agggcctgac | tcagactgac | 1380 |
| attctccact | tcttgttccc | cactgacagc | ctcccacccc | catctctccc | tcccctgcca | 1440 |
| ttttgggttt | tgggtctttg | aacccttgct | tgcaataggt | gtgcgtcaga | agcacccagg | 1500 |
| acttccattt | gctttgtccc | ggggctccac | tgaacaagtt | ggcctgcact | ggtgttttgt | 1560 |
| tgtggggagg | aggatgggga | gtaggacata | ccagcttaga | ttttaaggtt | tttactgtga | 1620 |
| gggatgtttg | ggagatgtaa | gaaatgttct | tgcagttaag | ggttagttta | caatcagcca | 1680 |
| cattctaggt | aggggcccac | ttcaccgtac | taaccaggga | agctgtccct | cactgttgaa | 1740 |
| ttttctctaa | cttcaaggcc | catatctgtg | aaatgctggc | atttgcacct | acctcacaga | 1800 |
| gtgcattgtg | agggttaatg | aaataatgta | catctggcct | tgaaaccacc | ttttattaca | 1860 |
| tggggtctag | aacttgaccc | ccttgagggt | gcttgttccc | tctccctgtt | ggtcggtggg | 1920 |

```
ttggtagttt ctacagttgg gcagctggtt aggtagaggg agttgtcaag tctctgctgg    1980
cccagccaaa ccctgtctga caacctcttg gtgaaccttc gtacctaaaa ggaaatctca    2040
ccccatccca caccctggag gatttcatct cttgtatatg atgatctgga tccaccaaga    2100
cttgttttat gctcagggtc aatttctttt ttctttttt ttttttttt tcttttctt      2160 tgagactggg tctcgctttg ttgcccaggc tggagtggag tggcgtgatc ttggcttact    2220
gcagcctttg cctccccggc tcgagcagtc ctgcctcagc ctccggagta gctgggacca    2280
caggttcatg ccaccatggc cagccaactt ttgcatgttt tgtagagatg gggtctcaca    2340
gtgttgccca ggctggtctc aaactcctgg gctcaggcga tccacctgtc tcagcctccc    2400
agagtgctgg gattacaatt gtgagccacc acgtccagct ggaagggtca acatcttta    2460 cattctgcaa gcacatctgc attttcaccc caccettccc ctccttctcc cttttttat    2520 cccatttta tatcgatctc ttattttaca ataaaacttt gctgccacct gtgtgtctga    2580
ggggtg                                                              2586
```

REPROGRAMMING METHOD FOR PRODUCING INDUCED PLURIPOTENT STEM CELLS (IPSC)

RELATED APPLICATION DATA

This application is a National Stage Application under 35 U.S.C. 371 of co-pending PCT application number PCT/EP2016/052085 designating the United States and filed Feb. 1, 2016; which claims the benefit of EP application number 15305145.3 and filed Jan. 30, 2015 each of which are hereby incorporated by reference in their entireties.

TECHNICAL FIELD OF THE INVENTION

The present application is in the field of cellular biology and more particularly, in the field of the stem cells. It relates to the method for reprogramming induced pluripotent stem cells (iPSC) comprising a transduction of somatic differentiated cells with vector expressing p53 isoform, to the induced pluripotent stem cells obtained by the method of the invention and their use. The present invention also relates to a method for detecting induced pluripotent stem cells (iPSC).

BACKGROUND ART

Induced pluripotent stem cells (also known as iPSCs) are a type of pluripotent stem cell generated directly from adult cells. The iPSC technology was pioneered by Japanese Shinya Yamanaka, demonstrating in 2006 that the introduction of four specific genes (Oct4, Sox2, cMyc and Nanog) encoding transcription factors could convert adult cells into pluripotent stem cells.

Currently, pluripotent stem cells hold great promise in the field of regenerative medicine. Its objectives are to repair tissues altered by accident, diseases or aging. This represents a new therapeutic field with tremendous medical impact because it offers the possibility to treat and cure diseases currently without adequate treatment. Regenerative medicine applies to most medical domains and constitutes one of the most promising developments of the biotechnology industry. Ischemic, degenerative and/or ageing-associated diseases are the major causes of mortality in the population of developed countries.

It is widely recognized that stem cells could be a source of cells for cellular therapy for these diseases because of their proliferative and differentiating capacity. However, medical applications of embryonic stem cells are hampered by immunological and ethical concerns.

These two obstacles are set aside by the iPSC (induced Pluripotent Stem Cell) technology.

iPSCs offer autologous cell sources for replacement cell therapy, to replace or regenerate tissues by autologous transplantation. Moreover, patient-specific iPSCs can serve as in vitro models for disease mechanism modeling and drug screening.

The original set of reprogramming factors (also called Yamanaka factors) comprises the genes Oct4, Sox2, cMyc and Nanog. More recently, some specific combinations including three of these factors were reported to also generate iPSC.

However, reprogramming of iPSC using these factors only occurs in a very small percentage of transfected cells demonstrating that the therapeutic use of iPSCs has to face many barriers among which safety, regulatory issues, financial viability, low reprogramming efficiency and an uncertain stability of derived iPSC.

Various solutions to the problem of low reprogramming efficiency have been proposed, based on the regulation of the expression (overexpression or inhibition) of other genes, in addition to at least some of the Yamanaka factors. However, the methods proposed in the prior art for increasing reprogramming efficiency generally result in DNA lesions and chromosomal aberrations, due to the concomitant induction of alterations in DNA repair machinery. As a result, while increasing reprogramming efficiency, proposed methods are not suitable for the preparation of high numbers of clinically useful iPSCs.

For instance, the original Yamanaka factors include c-myc, an oncogene that is known to alter DNA repair machinery and to result in DNA lesions and chromosomal aberrations. While this factor is in fact not necessary to induce iPSCs, using only the other Yamanaka factors results in decreased reprogramming efficiency.

Recent studies have documented the role of p53 in stem cell (SC) homeostasis and in pluripotency induction. p53 not only ensures genomic integrity after genotoxic insults but also controls SC proliferation and differentiation. Additionally, p53 exerts an effective barrier to the generation of iPSCs from terminally differentiated cells. If wild-type (wt) p53 has inhibitory effects, some p53 mutants display completely opposite effects (Sarig et al, 2010). A recent genome wide study demonstrated that p53 regulates approximately 3600 genes in mouse ES cells (Li et al, 2012). Out of these, about 2000 genes are positively regulated while 1600 are repressed. Positively regulated genes are enriched in genes responsible for differentiation while negatively regulated genes, in maintaining ES cell status. p53 represses key regulators of ES phenotype like Oct 4, Nanog, Sox2, c-myc (Li et al, 2012; Lin et al, 2005). Consequently, recent reports showed that p53 is an obstacle to cellular reprogramming through p21 signalling pathway (Hong et al, 2009).

It was found that the depletion of p53 significantly increased efficacy of cell reprogramming, concomitantly providing iPSC generated using only two factors (Sox2 and Oct 4) of the Yamanaka cocktail (Kawamura et al, 2009). Takenaka et al. also disclose that the inhibition of p53 allows obtaining iPSC from CD34+ monocytes (2010).

However, generating iPSC by p53 depletion or expression of mutated p53 proteins carries great risk due to the fact that these cells present tumor like features and develop malignant tumors when injected in mice. The permanent suppression of p53 may thus lower the quality of iPSCs, in particular by accumulating DNA lesions and chromosomal aberrations during iPSC derivation and maintenance (Tapia & Scholer, 2010). So the use in cell therapy of iPSC obtained by the depletion of p53 genes or the expression of mutated p53 proteins is hazardous and unsure.

Otherwise, the TP53 gene encodes at least twelve different physiological isoforms [TAp53 ($\alpha$, $\beta$ and $\gamma$), $\Delta$40p53 ($\alpha$, $\beta$ and $\gamma$), $\Delta$133p53 ($\alpha$, $\beta$ and $\gamma$) and $\Delta$160p53 ($\alpha$, $\beta$ and $\gamma$)] (Bourdon, 2007) via several mechanisms: use of alternative promoters (the TA and $\Delta$133 isoforms), alternative intron splicing (intron 2: $\Delta$40 isoforms and intron 9: $\alpha$, $\beta$ and $\gamma$ isoforms) and alternative translational initiation sites ($\Delta$40 isoforms and $\Delta$160 isoforms). A scheme summarizing the features of isoforms $\alpha$, $\beta$ and $\gamma$ of TAp53, $\Delta$40p53, and $\Delta$133p53 is presented in FIG. 1. The TAp53$\alpha$ isoform is the best described and classically mentioned in the literature as p53. Basically, p53 isoforms can be divided in two groups: long isoforms that contain the transactivation domain (TA and $\Delta$40) and short isoforms without transactivation domain (Δ133 and Δ160). Furthermore, the β and γ isoforms do not contain the canonical C-terminal oligomerization domain, but an additional domain with unknown function(s) to date (Khoury and Bourdon, 2011). p53 isoforms can regulate p53 transcriptional activity and have different outcomes on cell fate by regulating cell cycle progression, programmed cell death, replicative senescence, viral replication, cell differentiation and angiogenesis (Aoubala et al, 2011; Bourdon et al, 2005; Hofstetter et al, 2012; Nutthasirikul et al, 2013; Terrier et al, 2012).

WO 2012/044979 discloses the use of Δ133p53α isoform for increasing reprogramming efficiency and thus iPSCs induction in the presence of at least one reprogramming factor selected from Yamanaka factors. However, this document contains no data showing that iPSC obtained with the method disclosed are genetically stable and do not have DNA damages or alterations in DNA repair machinery. Consequently, there is still a need for methods allowing efficient reprogramming of somatic cells to induced pluripotent stem cells (iPSC) that are free of genetic damages and have normal somatic cells functions and in particular an unaltered DNA repair machinery, thus guaranteeing their genetic stability and their possible clinical use.

SUMMARY OF THE INVENTION

In the context of the present invention, the inventors have now found that Δ133p53β isoform and/or Δ133p53γ is involved in stem cell reprogramming. Particularly, Δ133p53β and/or Δ133p53γ isoforms is (are) able to induce stem cell reprogramming of somatic differentiated cells in the absence of heterologous induction of any of the Yamanaka transcription factors (Oct4, Sox2, cMyc and Nanog) or without depleting or inducing mutations in p53 genes. The overexpression of these isoforms does not alter DNA in the reprogrammed iPSC. Moreover, DNA repair checkpoint response also remains functional.

The inventors further demonstrated that among Δ133p53 isoforms, only isoforms β and γ are able to induce a reprogramming in the absence of all Yamanaka factors, the expression of Δ133p53α isoform not permitting to induce iPSCs in the absence of Yamanaka factors. They further demonstrated that expression of Δ133p53β isoform does not alter the DNA repair machinery of reprogrammed iPSCs, contrary to expression of Δ133p53α isoform, the expression of which results in decrease of the accumulation of p21WAF1 in the presence of DNA damage, indicating that the DNA repair function of p53 is altered in cells expressing Δ133p53α isoform.

These findings were unexpected since, as far as the inventors know, the expression of p53 isoforms Δ133p53β and/or Δ133p53γ in stem cells, particularly in induced pluripotent stem cells has never been described before the present invention. In particular, it had not been shown that expression of p53 isoforms Δ133p53β and/or Δ133p53γ in somatic cells in the absence of all Yamanaka factors permitted to reprogram such somatic cells into iPSCs. Moreover, the findings of the inventors were unexpected since WO 2012/044979 discloses that expression of Δ133p53α isoform allows increasing reprogramming efficiency only in the presence of at least one of the Yamanaka factors, which has been confirmed by the inventors, who demonstrate that this particular isoform does not allow inducing iPSC from somatic cells when used alone (in the absence of all Yamanaka factors) and that its expression alters DNA repair mechanisms. The fact that expression of Δ133p53β and/or Δ133p53γ isoforms do not alter the DNA repair machinery of reprogrammed iPSCs indicates that—these isoforms will preserves genetic stability.

The above findings allow to overcome the drawbacks occurring in the prior art since there is no need to express several transcriptional factors in order to reprogramm somatic cells into iPSCs, or to deplete p53 or use constructs with mutations in p53 encoding genes. The new method provided by the inventors thus at the same time improved reprogramming efficiency and decreases the risk of genetic instability due to alteration of DNA repair mechanisms. Consequently, this finding allows the generation of induced stem cells with better efficiency, genomic stability without DNA alterations.

In a first aspect, the present invention thus relates to a reprogramming method induced pluripotent stem cells (iPSC) comprising
  a) transducing somatic differentiated cells with a vector expressing Δ133p53β, Δ133p53γ, or both Δ133p53β and Δ133p53γ isoforms;
  b) culturing transduced somatic differentiated cells in a medium supporting their expansion; and
  c) isolating induced pluripotent stem cells (iPSC).

The inventor demonstrated that both Δ133p53β and Δ133p53γ isoforms (but not Δ133p53α), and particularly Δ133p53β are highly expressed in the obtained iPSC. A high expression indicates that an elevated level of these isoforms is not associated with genetic instability or alteration of the DNA repair response, contrary to the one due to the overexpression of Yamanaka transcription factors or to the depletion or the expression of mutated p53 proteins. Consequently, using physiological p53 isoforms in the reprogramming method of the present invention allows reducing the risk of genetic alteration because the Δ133p53β isoforms do not alter the DNA repair response) and thus obtaining induced pluripotent stem cells with better efficiency and stability, which may be used in cell therapy.

In a second aspect, the present invention thus relates to induced pluripotent stem cells (iPSC) obtained by the reprogramming method of the invention. The iPSC obtained by the method of the invention contain the vector expressing Δ133p53β and/or Δ133p53γ isoforms.

Due to their better stability and their undamaged DNA repair functions, such iPSC may be used in cell therapy and/or as in vitro model to study a variety of diseases.

In a third aspect, the present invention thus relates to iPSC as obtained from the reprogramming method of the invention for use in cell therapy and/or as models to study a variety of diseases.

The finding that induced pluripotent stem cells specifically express Δ133p53β isoform, Δ133p53γ isoform, or both Δ133p53β and Δ133p53γ isoforms also allows detecting iPSC by detecting Δ133p53β, Δ133p53γ isoform, or both Δ133p53β and Δ133p53γ isoforms in a cell population containing iPSC.

In a fourth aspect, the present invention thus relates to a method for detecting Induced pluripotent stem cells (iPSC) comprising detecting the presence of Δ133p53β isoform Δ133p53γ isoform, or both Δ133p53β and Δ133p53γ isoforms by detecting Δ133p53β isoform, Δ133p53γ isoform, or both Δ133p53β and Δ133p53γ isoforms polypeptide and/or a fragment thereof, and/or by detecting Δ133p53β, Δ133p53γ isoform, or both Δ133p53β and Δ133p53γ isoforms mRNA and/or a fragment thereof.

DETAILED DESCRIPTION OF THE INVENTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

P53 Isoforms

Figure 1:
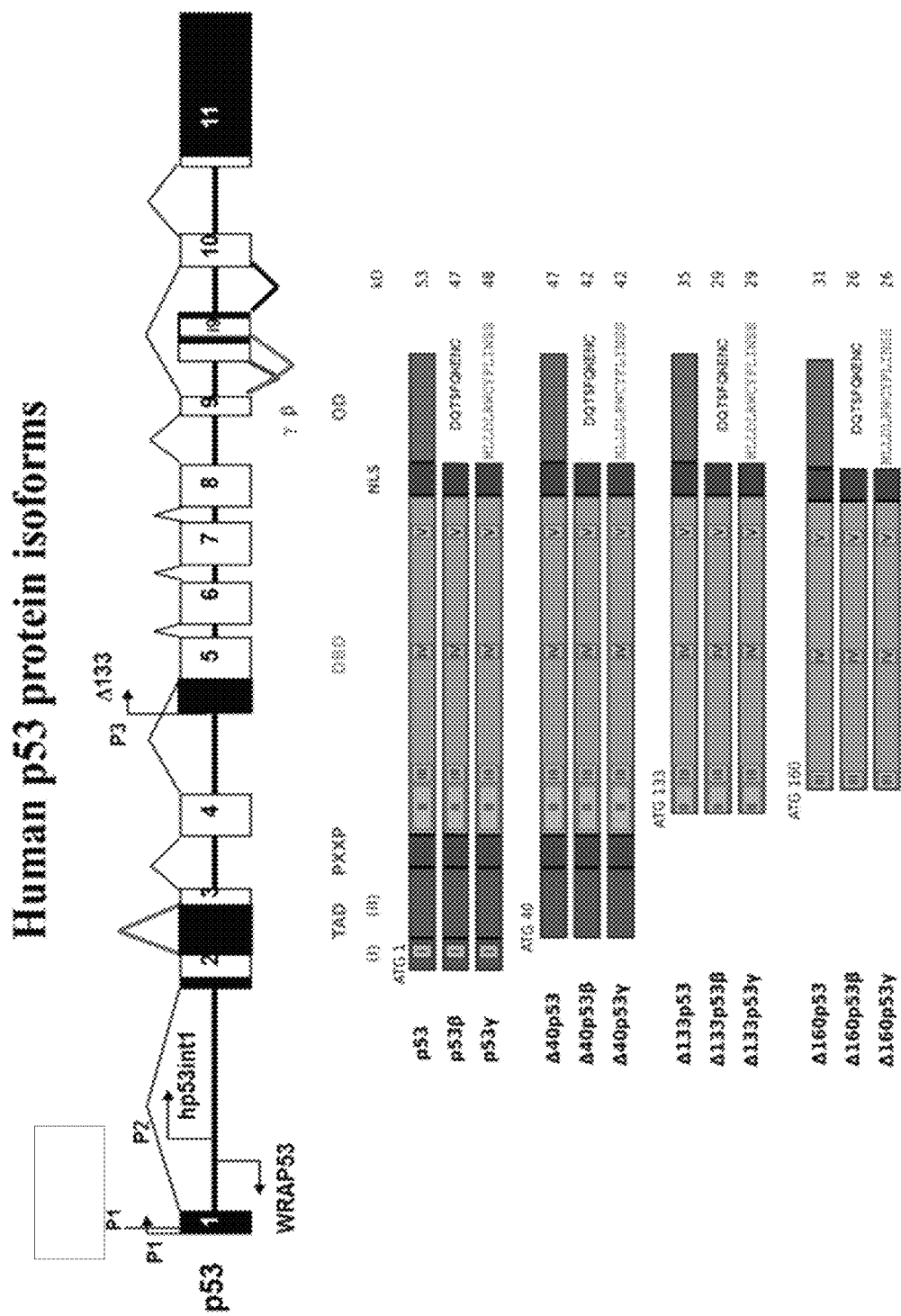
FIG. 1: Schematic representation of human p53 isoforms. The human p53 gene contains a proximal (P1) and an internal (P2) promoter, regulating the expression of p53 and Δ133p53 transcripts, respectively. The p53 transcript encodes two p53 isoforms: p53 and Δ40p53, produced by internal initiation of translation using ATG 40. The p53 gene expresses three alternatively spliced carboxy-terminal isoforms (α, β and γ). p53β and p53γ protein isoforms differ from full-length p53 (FLp53) in that they lack the classical oligomerization domain. The Δ133p53 transcript encodes both Δ133p53 and Δ160p53 isoforms, which combined with the alternatively spliced α☐☐β☐ and ☐γ.exons generates Δ133p53α Δ133p53β, Δ133p53γ and Δ160p53α Δ160p53β, Δ160p53γ (Bourdon et al, 2005; Marcel et al, 2010). These isoforms are deleted of the N-terminal transactivation domains and part of the DNA-binding domain.

P53 isoforms are presented in FIG. 1.

In addition, Table 1 below provides amino acids and nucleic acid sequences of full-length p53 (denoted as "p53"), and of Δ133p53β and Δ133p53γ isoforms.

TABLE 1

Amino acids and nucleic acid sequences of full-length p53 (denoted as "p53"), and of Δ133p53β and Δ133p53γ isoforms.

| Isoform | Amino acids sequence (SEQ ID NO:/Genbank accession number) | Nucleic acid sequence (SEQ ID NO:/Genbank accession number) |
|---|---|---|
| Δ133p53β | SEQ ID NO: 1/ NP_001119588.1 | SEQ ID NO: 2/ NM_001126116.1 |
| Δ133p53γ | SEQ ID NO: 3/ NP_001119589.1 | SEQ ID NO: 4/ NM_001126117.1 |
| p53 | SEQ ID NO: 5/ NP_000537.3 | SEQ ID NO: 6/ NM_000546.4 |

Induced Pluripotent Stem Cells (iPSC) and Somatic Differentiated Cells

In the present description, "induced pluripotent stem cells" or "iPSC" refer to pluripotent stem cells obtained from a non-pluripotent cell, typically an adult somatic cell (a cell of the body, rather than gametes or an embryo), by inducing a "forced" expression of certain genes. iPSCs are believed to be similar to natural pluripotent stem cells, such as embryo stem cells (ESCs) in many respects. iPSCs are not adult stem cells, but reprogrammed cells given pluripotent capabilities. iPSCs do not refer to cells as they are found in nature.

In the present description, "somatic cells" or "somatic differentiated cell" refer to differentiated adult cells. As used in the present application, the somatic cells or somatic differentiated cells may be non-cancerous (also called "normal cells") or cancerous cells. Preferably, the somatic cells or somatic differentiated cells used in the present application are non-cancerous cells.

In the present description, "reprogramming", refers to a process that alters or reverses the differentiation status of a somatic cell that is either partially or terminally differentiated.

In the present description, "DNA damage" refers to an alteration in the chemical structure of DNA, such as a single stranded or double stranded DNA break ithat may be cause by internal or external agents. Damage to DNA may occur naturally as a result of metabolic alterations (leading to increased production of reactive oxygen species, reactive nitrogen species, reactive carbonyl species, lipid peroxidation products and alkylating agents) can result from metabolic (metabolism releases compounds that damage DNA including reactive oxygen species, reactive nitrogen species, reactive carbonyl species, lipid peroxidation products and alkylating agents) or hydrolytic processes (leading to cleavage of chemical bonds in DNA). DNA damage may also be caused by external factors like UV exposition or gamma irradiations.

In the present description, "DNA repair" or "DNA repair checkpoint response" or just "DNA repair response" or "DNA repair mechanisms" or "DNA repair machinery" refers to several processes by which a cell identifies and corrects the DNA damage. For each type of DNA damage, the cell has evolved a specific method of repairing the damage or eliminating the damaging compound. Various cell proteins are known to be involved in DNA repair and may thus be tested in order to determine the presence or absence of DNA repair alterations in a given cell. Examples of such proteins known to be involved in DNA repair include two p53 targets: p21WAF-1 (inhibitors of cyclin complex/Cdks) and Mdm2 (proteins involved in p53 degradation).

Vectors

A "plasmid vector" as used herein refers to a replicable DNA construct.

The term "viral vector" as used herein refers to a nucleic acid vector that includes at least one element of a virus genome and may be packaged into a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject.

As used herein, the term "regulatory elements" or "regulatory sequence" refers to any element that allows, contributes or modulates the expression of nucleic acid molecule(s) in a given host cell or subject, including replication, duplication, transcription, splicing, translation, stability and/or transport of the nucleic acid(s) or its derivative (i.e. mRNA).

Other Definitions

In the present description, "an aging-associated disease" refers to a disease that is seen with increasing frequency with increasing senescence. Age-associated diseases are to be distinguished from the aging process itself because all adult humans age, but not all adult humans experience all age-associated diseases.

In the present description, "degenerative diseases" refers to medical problems that worsen over time. These degenerative diseases may affect the central nervous system (brain and spinal cord), bones, blood vessels or heart.

Reprogramming Method for Inducing Pluripotent Stem Cells (iPSC)

In the context of the present invention the inventors have found that Δ133p53β isoform, Δ133p53γ isoform, or both Δ133p53β and Δ133p53γ isoforms have the capacity:

- to induce phenotypic changes similar to those activated during cell reprogramming, in the absence of all Yamanaka reprogramming factors);
- to confer pluripotency to differentiated cell, indicating that this isoform recapitulates the activities of the set of reprogramming factors (Sox 2, Oct ¾, Nanog and c-Myc);
- to induce iPSC without causing damages to the DNA structure and function, thus maintaining its stability;
- to induce iPSC without altering DNA repair mechanisms.

These findings are very important since they provide a simple mean (the reprogramming method of the invention) for producing induced pluripotent stem cells with high efficiency and stability, without causing damaged DNA and retaining intact DNA repair mechanisms, thus making them useful in cell therapy.

In a first aspect, the present invention thus relates to a reprogramming method for producing induced pluripotent stem cells (iPSC), comprising:

a) transducing somatic differentiated cells with a vector expressing Δ133p53β isoform, Δ133p53γ isoform, or both Δ133p53β and Δ133p53γ isoforms;

b) culturing transduced somatic differentiated cells in a medium supporting their expansion; and c) isolating induced pluripotent stem cells.

The reprogramming method of the present invention is an in vitro method.

In an embodiment, the reprogramming method of the invention does not comprise a step of expression of Yamanaka transcription factors (Oct4, Sox2, cMyc and Nanog) or a depletion of p53 or an expression of p53 mutated proteins. In other words, in this embodiment, the somatic differentiated cells are not and have not been previously transduced with one or more vector(s) expressing one or more of Yamanaka transcription factors (Oct4, Sox2, cMyc and Nanog), one or more p53 mutated proteins, or an inhibitor of p53.

Somatic Differentiated Cells

Somatic dedifferentiated cells for use with the reprogramming method of the present invention may be primary cells or immortalized cells. Such cells may be primary cells (non-immortalized cells), such as those freshly isolated from an animal, or may be derived from a cell line (immortalized cells). The somatic cells are mammalian cells, such as, for example, human cells or mouse cells. They may be obtained by well-known methods, from different organs, such as, but not limited to skin, lung, pancreas, liver, stomach, intestine, heart, reproductive organs, bladder, kidney, urethra and other urinary organs, or generally from any organ or tissue containing living somatic cells. Mammalian somatic cells useful in the present invention include, by way of example, adult stem cells, Sertoli cells, endothelial cells, granulosa epithelial cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, other known muscle cells, and generally any live somatic cells. These cells may be non-cancerous or cancerous cell, preferably these cells are non-cancerous cells.

Preferably, the somatic differentiated stem cells used with the reprogramming method of the invention are selected from the group consisting of human peripheral blood mononuclear cells (PBMC), CD4+ lymphocytes or fibroblasts. More preferably, the somatic differentiated cells are human fibroblasts.

Isoform

In a preferred embodiment of the method for producing induced pluripotent stem cells according to the invention, it is the Δ133p53β isoform, Δ133p53γ isoform or both Δ133p53β and Δ133p53γ isoforms (preferably only the Δ133p53β isoform) that is/are transduced in somatic differentiated cells in step b). Indeed, expression of Δ133p53β isoform is particularly associated to induction of pluripotent stem cells.

Vector Expressing Δ133p53β Isoform, Δ133p53γ Isoform, or Both Δ133p53β and Δ133p53γ Isoforms (Step b)

Any appropriate vector expressing Δ133p53β isoform, Δ133p53γ isoform, or both Δ133p53β and Δ133p53γ isoforms may be used.

A suitable vector comprises a nucleic acid molecule encoding Δ133p53β isoform, Δ133p53γ isoform, or both Δ133p53β and Δ133p53γ isoforms and elements necessary to allow expression thereof.

Suitable vectors notably include plasmid vectors and viral vectors.

Viral vectors can be replication-competent or -selective (e.g. engineered to replicate better or selectively in specific host cells), or can be genetically disabled so as to be replication-defective or replication-impaired. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the artisan to apply them.

In an embodiment, a plasmid vector expressing Δ133p53β isoform, Δ133p53γ isoform, or both Δ133p53β and Δ133p53γ isoforms is used.

Representative examples of suitable plasmid vectors include, without limitation, pREP4, pCEP4 (Invitrogen), pCI (Promega), pVAX (Invitrogen) and pGWiz (Gene Therapy System Inc).

For transduction, a plasmid vector may be complexed to lipids or polymers to form particulate structures such as liposomes, lipoplexes or nanoparticles.

In a preferred embodiment, a viral vector expressing Δ133p53β isoform, Δ133p53γ isoform, or both Δ133p53β and Δ133p53γ isoforms is used (i.e a viral vector comprising a nucleic acid molecule encoding Δ133p53β isoform, Δ133p53γ isoform, or both Δ133p53β and Δ133p53γ isoforms and elements necessary to allow expression thereof).

Representative examples of suitable viral vectors are generated from a variety of different viruses (e.g. retrovirus, adenovirus, adenovirus-associated virus (AAV), poxvirus, herpes virus, measles virus, foamy virus, alphavirus, vesicular stomatis virus, etc). As described above, the term "viral vector" encompasses vector DNA, genomic DNA as well as viral particles generated thereof, and especially infectious viral particles.

In a preferred embodiment, a retroviral vector expressing Δ133p53β isoform, Δ133p53γ isoform, or both Δ133p53β and Δ133p53γ isoforms isoform is used (i.e a retroviral vector comprising a nucleic acid molecule encoding Δ133p53β isoform, Δ133p53γ isoform, or both Δ133p53β and Δ133p53γ isoforms and elements necessary to allow expression thereof).

Retroviruses have the property of infecting, and in most cases integrating into, dividing cells and in this regard are particularly appropriate for use in the context of the present invention for producing induced pluripotent stem cells. A suitable retrovirus generally contains the LTR sequences, an encapsidation region and a nucleic acid molecule encoding Δ133p53β or Δ133p53γ isoform. The recombinant retrovirus can be derived from a retrovirus of any origin (murine, primate, feline, human, etc.) and in particular from the MoMuLV (Moloney murine leukemia virus), MVS (Murine sarcoma virus), Friend murine retrovirus (Fb29), Murine Embryonic Stem Cell Virus (MESV), LN virus or Murine Stem Cell Virus (MSCV). It is propagated in an encapsidation cell line which is able to supply in trans the viral polypeptides gag, pol and/or env which are required for constituting a viral particle. Such cell lines are described in the literature (PA317, Psi CRIP GP+Am-12, HEK 293T etc.). The retroviral vector according to the invention can contain modifications, in particular in the LTRs (replacement of the promoter region with a eukaryotic promoter) or the encapsidation region (replacement with a heterologous encapsidation region).

In a particularly preferred embodiment, the vector used for transducing cancer cells in step b) is a Murine Stem Cell Virus (MSCV), which is derived from the Murine Embryonic Stem Cell Virus (MESV) and the LN retroviral vectors (Grez, M., et al. 1990; Miller, A. D. et al. 1989). Notably, the transducing vector may be obtained by cloning a molecule encoding Δ133p53β isoform, Δ133p53γ isoform, or both Δ133p53β and Δ133p53γ isoforms into a pMSCV vector commercialized by Clontech, such as pMSCVhyg, pMSCVneo, or pMSCVpuro.

However, other types of viral vectors expressing Δ133p53β isoform, Δ133p53γ isoform, or both Δ133p53β and Δ133p53γ isoforms may be used.

Examples of viral vectors that are useful in the context of the invention include adenoviral vectors, which may be derived from a variety of human or animal sources (e.g. canine, ovine, simian adenovirus, etc). Any serotype can be employed with a special preference for human adenoviruses and a specific preference for subgenus C such as Ad2, Ad5, Ad6, and subgenus B such as Ad11, Ad34 and Ad35. The cited adenovirus are available from ATCC or have been the subject of numerous publications describing their sequence, organization and methods of producing, allowing the artisan to apply them. When an adenoviral vector is used, it is preferably an E1-defective adenoviral vector with an E1 deletion extending from approximately positions 459 to 3328 or from approximately positions 459 to 3510 (by reference to the sequence of Ad5 disclosed in the GenBank under the accession number M73260.1). The cloning capacity can further be improved by deleting additional portion(s) of the adenoviral genome (all or part of the non-essential E3 region (e.g. deletion from approximately positions 27867 to 30743) or of other essential E2 and/or E4 regions. The nucleic acid molecule encoding Δ133p53β isoform, Δ133p53γ isoform, or both Δ133p53β and Δ133p53γ isoforms can then be inserted in any location of the adenoviral genome, with a specific preference for insertion in replacement of the E1 and/or E3 region. They may be positioned in sense or antisense orientation relative to the natural transcriptional direction of the region in question.

Other examples of viral vectors that may be used in the context of the invention include poxvirus vectors such as fowlpox vectors (e.g. FP9), canarypox vectors (e.g. ALVAC) and vaccinia virus vectors, the latter being preferred. Suitable vaccinia viruses include without limitation the Copenhagen strain, the Wyeth strain, NYVAC and the modified Ankara (MVA) strain. The general conditions for constructing and producing recombinant poxvirus are well known in the art. The nucleic acid molecule encoding Δ133p53β isoform, Δ133p53γ isoform, or both Δ133p53β and Δ133p53γ isoforms is preferably inserted within the poxviral genome in a non-essential locus. Thymidine kinase gene is particularly appropriate for insertion in Copenhagen vaccinia vectors and deletion II or III for insertion in MVA vector.

Other viral vectors suitable in the context of the invention are morbillivirus which can be obtained from the paramyxoviridae family, with a specific preference for measles virus. Insertion of the nucleic acid molecule encoding Δ133p53β isoform, Δ133p53γ isoform, or both Δ133p53β and Δ133p53γ isoforms between P and M genes or between H and L genes is particularly appropriate.

In the above vectors, the nucleic acid molecule encoding Δ133p53β isoform, Δ133p53γ isoform, or both Δ133p53β and Δ133p53γ isoforms are in a form suitable for expression in somatic cells, which means that each of the nucleic acid molecules set forth herein is operably linked to appropriate regulatory sequences.

It will be appreciated by those skilled in the art that the choice of the regulatory sequences can depend on such factors as the vector itself and the somatic cells to be transduced, and will be easily selected by those skilled in the art based on common general knowledge and publications on this topic. Suitable promoters for constitutive expression in eukaryotic systems include viral promoters, such as SV40 promoter, the cytomegalovirus (CMV) immediate early promoter or enhancer, the adenovirus early and late promoters, the thymidine kinase (TK) promoter of herpes simplex virus (HSV)-1 and retroviral long-terminal repeats (e.g. MoMuLV and Rous sarcoma virus (RSV) LTRs) as well as cellular promoters such as the phosphoglycero kinase (PGK) promoter. Examples of suitable promoters for a Murine Stem Cell Virus (MSCV) vector include those present in pMSCV vector commercialized by Clontech, such as pMSCVhyg, pMSCVneo, or pMSCVpuro.

In step b), transduced somatic differentiated cells are cultured in a medium supporting their expansion. Such a medium may be a basal medium (comprising inorganic salts, amino acids, vitamins and glucose, such as DMEM), which may be supplemented with a reducing agent (such as β-mercaptoethanol), at least one antibiotic (such as Penicillin-Streptomycin), and/or at least one growth factor able to sustain expansion of the type of transduced somatic differentiated cells (including, but not limited to, Epidermal Growth Factor (EGF) and/or basic Fibroblast Growth Factor (bFGF)).

Step b) is performed for a period sufficient in order to recover induced pluripotent stem cells from the transduced somatic differentiated cell culture. A suitable period should be optimized for each type of somatic differentiated cells, but will generally be between 3 and 30 days, in particular between 7 and 20 days, more particularly, between 9 and 24 days.

In order to obtain iPSC having genetic stability (i.e. without DNA damages or damages of DNA repair response) by the method of the present invention, it is necessary to transduce somatic differential cells with at least one of $\Delta 133p53\beta$ isoform or $\Delta 133p53\gamma$ isoform or both isoforms, preferably with $\Delta 133p53\beta$ isoform.

Isolation of Induced Pluripotent Stem Cells (Step c) In step c), induced pluripotent stem cells are isolated from the transduced somatic differentiated cells culture.

In the transduced somatic differentiated cells culture, induced pluripotent stem cells may be isolated based on selection of any feature specific to induced pluripotent stem cells compared to other somatic differentiated cells.

In particular, depending on the type of somatic differentiated cells, iPSCs can be identified and isolated by any one of means of:
  i) isolation according to iPSC-specific cell surface markers;
  ii) isolation by flow cytometry based on side-population (SP) phenotype by DNA dye exclusion;
  iii) embryoid body formation, and
  iv) iPSC colony picking.

In method i), iPSCs are isolated based on iPSC-specific cell surface markers. In this method, transduced differentiated somatic cells are stained using antibodies directed to one or more iPSC-specific cell surface markers, and cells having the desired surface marker phenotype are sorted. Those skilled in the art know how to implement such isolation based on surface cell markers. For instance, flow cytometry cell-sorting may be used, transduced somatic cells are directly or indirectly fluorescently stained with antibodies directed to one or more iPSC-specific cell surface markers and cells by detected by flow cytometer laser as having the desired surface marker phenotype are sorted. In another embodiment, magnetic separation may be used. In this case, antibody labelled transduced somatic cells (which correspond to iPSCs if an antibody directed to a iPSC marker is used, or to non-iPSC if an antibody specifically not expressed by iPSCs is used) are contacted with magnetic beads specifically binding to the antibody (for instance via avidin/biotin interaction, or via antibody-antigen binding) and separated from antibody non-labelled transduced somatic cells. Several rounds of magnetic purification may be used based on markers specifically expressed and non-expressed by iPSCs.

The most common surface markers used to distinguish iPSCs are SSEA3, SSEA4, TRA-1-60, and TRA-1-81. The expression of SSEA3 and SSEA4 by reprogramming cells usually precedes the expression of TRA-1-60 and TRA-1-81, which are detected only at later stages of reprogramming. It has been proposed that the antibodies specific for the TRA-1-60 and TRA-1-81 antigens recognize distinct and unique epitopes on the same large glycoprotein Podocalyxin (also called podocalyxin-like, PODXL)1. Other surface modifications including the presence of specific lectins have also been shown to distinguish iPSCs from non-iPSCs. Several CD molecules have been associated with pluripotency such as CD30 (tumor necrosis factor receptor superfamily, member 8, TNFRSF8), CD9 (leukocyte antigen, MIC3), CD50 (intercellular adhesion molecule-3, ICAM3), CD200 (MRC OX-2 antigen, MOX2) and CD90 (Thy-1 cell surface antigen, THY1). It also possible to distinguish iPSC by negative selection with CD44. Furthermore iPSC may be selected by the expression of the Yamanaka transcription factors (Oct4, Sox2, cMyc and Nanog).

The skilled artisan knows adapt the selection protocol by using one or more of different surface markers of iPSC well known in the art.

In method ii), iPSCs are isolated by flow cytometry cell-sorting based on DNA dye side population (SP) phenotype. This method is based on the passive uptake of cell-permeable DNA dyes by live cells and pumping out of such DNA dyes by a side population of stem cells via ATP-Binding Cassette (ABC) transporters allowing the observation of a side population that has a low DNA dye fluorescence at the appropriate wavelength. ABC pumps can be specifically inhibited by drugs such as verapamil (100 µM final concentration) or reserpine (5 µM final concentration), and these drugs may be used to generate control samples, in which no SP phenotype may be detected. Appropriate cell-permeable DNA dyes that may be used include Hoechst 33342 (the main used DNA dye for this purpose, see Golebiewska et al., 2011) and Vybrant® DyeCycle™ stains available in various fluorescences (violet, green, and orange; see Telford et al-2010).

In method iii), iPSC are isolated by embryoid body (EB) formation. Embryoid bodies (EB) are the three dimensional aggregates formed in suspension by induced pluripotent stem cells (iPSC). There are several protocols to generate embryoid bodies and those skilled in the art know how to implement such isolation based on embryoid body formation. Communally, the cell population containing iPSC is cultured previously by the embryoid formation. in appropriate culture medium. On the day of EB formation when the cells grow to 60-80% confluence, cells are washed and then incubated in EDTA/PBS for 3-15 minutes to dissociate colonies to cell clumps or single cells according to EB formation methods. Often, the aggregate formation is induced by using different reagents. According to used protocol it is possible to obtain different EB formation such as self-aggregated EBs, hanging drop EBs, EBs in AggreWells ect (Lin et al., 2014).

In the method iv), iPSC are isolated by iPSC colony picking. A protocol for iPSC colony picking is described in the Examples given below. However, skilled artisan may implement other protocols of iPSC colony picking well known in the art.

According to preferred embodiment, the reprogramming method of the present invention comprises, before the step a), a step a1) of isolating and culturing the somatic pluripotent cells which will be transduced with the expression vector.

Preferably, step a1) is performed about 2 days before step a) by culturing the somatic differentiated cells in appropriate cell medium in order to achieve 50 to 80%, particularly, 60 to 70% of confluency. For example, such culture medium is provided with «Invitrogen kit»: CytoTune®-iPS 2.0 Sendai Reprogramming Kit (Catalog Numbers A16517, A16518).

According to another preferred embodiment of the reprogramming method of the invention, after step a) the viruses are removed of transduced somatic differentiated cells by replacing the cell medium with fresh cell medium.

Induced Pluripotent Stem Cells (iPSC) Obtained by the Reprogramming Method of the Invention and Uses Thereof In a second aspect, the present invention relates to induced pluripotent stem cells (iPSC) obtained by the reprogramming method of the invention. The reprogramming method of the invention does not require performing (and in one embodiment does not comprise) a step of expression of Yamanaka transcription factors (Oct4, Sox2, cMyc and Nanog) or a depletion of p53 or an expression of p53 mutated proteins, and the iPSC obtained by the reprogramming method of the invention are stable and non-cancerous and have better capacity to be re-differentiated in non-cancerous somatic multipotent, unipotent or differentiated somatic cells. The genetic stability of the iPSC obtained by the method of the invention is preserved because of the use of one of these or both Δ133p53β and Δ133p53γ isoforms since their expression does not create DNA damage DNA, and also does not alter DNA repair mechanisms.

The iPSC produced by the method of the invention contain the expression vector encoding Δ133p53β and/or Δ133p53γ isoforms. The iPSC produced by the method of the invention also express Δ133p53β and/or Δ133p53γ isoforms.

Preferably, the iPSC obtained from reprogramming method of the present invention may be differentiated to hematopoietic stem cells.

In another aspect, the iPSCs as produced by the reprogramming method of the invention are used in cell therapy.

According to a preferred embodiment, the iPSCs produced by the reprogramming method of the invention are used as therapeutic agent in the treatment of aging-associated and/or degenerative diseases.

Examples of aging-associated diseases are diseases selected from the group comprising or consisting of atherosclerosis, cardiovascular disease, cancer, arthritis, cataracts, osteoporosis, type 2 diabetes, hypertension, Alzheimer's disease and Parkinson disease.

Examples of degenerative diseases are diseases selected from the group comprising or consisting of diseases affecting the central nervous system (Alzheimer's disease and Parkinson disease, Huntington diseases), bones (Duchene and Becker muscular dystrophies), blood vessels or heart.

According to the preferred embodiment of the invention, the iPSCs produced by the reprogramming method of the invention are used as therapeutic agent for the treatment of aging-associated and degenerative diseases selected from the group consisting of cardiovascular diseases, diabetes, cancer, arthritis, hypertension, myocardial infection, strokes, amyotrophic lateral sclerosis, Alzheimer's disease and Parkinson disease.

In another aspect of the invention, the iPSCs produced by the reprogramming method of the invention are used in vitro as model for studying diseases selected from the group comprising or consisting of amyotrophic lateral sclerosis, adenosine deaminase deficiency-related severe combined immunodeficiency, Shwachman-Bodian-Diamond syndrome, Gaucher disease type III, Duchene and Becker muscular dystrophies, Parkinson's disease, Huntington's disease, type 1 diabetes mellitus, Down syndrome and spinal muscular atrophy.

As mentioned above, the Inventors have found that Δ133p53β isoform, Δ133p53γ isoform or both Δ133p53β and Δ133p53γ are specifically expressed in iPSC.

A Method for Detecting Induced Pluripotent Stem Cells (iPSC)

In further aspect, the invention thus relates to a method for detecting Induced pluripotent stem cells (iPSC) in cell population comprising detecting the presence of Δ133p53β isoform, Δ133p53γ isoform or both Δ133p53β and Δ133p53γ by detecting a Δ133p53β, Δ133p53γ isoform or both Δ133p53β and Δ133p53γ isoform polypeptide and/or a fragment thereof, and/or by detecting a Δ133p53β isoform, Δ133p53γ isoform or both Δ133p53β and Δ133p53γ mRNA and/or a fragment thereof.

According to a preferred embodiment, the detecting method according to the invention is based on detecting the presence of Δ133p53β isoform. The detecting of presence of Δ133p53β isoform is carried out by using a probe capable of specifically hybridizing with said Δ133p53β isoform mRNA, complementary sequence thereof or a fragment thereof having at least 10, 15, 20, 25, 30, 35, 40, 45, 50 or more nucleotides length which is specific of said Δ133p53β isoform.

Such probes and fragments are described in international patent application WO2011/000891 (the probes and fragments preferably hybridizing with Δ133p53β isoform mRNA having the sequence SEQ ID NO: 2) and may be used in the method for detecting Induced pluripotent stem cells (iPSC) of the present invention.

Furthermore, the presence of Δ133p53γ isoform may be also detected by using a probe capable of specifically hybridizing with said Δ133p53γ isoform mRNA, complementary sequence thereof or a fragment thereof having at least 10, 15, 20, 25, 30, 35, 40, 45, 50 or more nucleotides length which is specific of said Δ133p53γ isoform.

Such probes and fragments are also described in international patent application WO2011/000891 (the probes and fragments preferably hybridizing with Δ133p53β isoform mRNA having the sequence SEQ ID NO: 6) and may be used in the method for detecting Induced pluripotent stem cells (iPSC) of the present invention.

EXAMPLES

Materials and Methods

The following is a description of materials and methods used in following examples.

The reprogramming method for iPS production by the human Δ133p53β isoforms is adapted from the «Invitrogen kit»: CytoTune®-iPS 2.0 Sendai Reprogramming Kit (Catalog Numbers A16517, A16518). For controls of reprogramming, the above mentioned kit will be used according to the manufacturer instructions as follows:

Culturing of human fibroblasts

On Day −2: human fibroblasts (established from normal human foreskin) was plated with a passage number of 5 or lower into at least two wells of a 6-well plate in fibroblast medium so that they are 50-80% confluent on the day of transduction (Day 0).

For 100 mL of complete MEF/fibroblast medium, the following components were mixed:
DMEM 89 mL
FBS, ESC-Qualified 10 mL
MEM Non-Essential Amino Acids Solution, 10 mM 1 mL
β-mercaptoethanol, 55 mM 100 μL Transducing the human fibroblast previously cultured with different viral vectors On Day 0: the fibroblasts were transduced with the CytoTuneR 2.0 Sendai reprogramming vectors control probe and with the vectors expressing Δ133p53 isoforms (β and γ) at the appropriate MOI. The cells were incubated overnight.

On Day 1: the medium was replaced with fresh complete fibroblast medium to remove the
viral vectors.

On Day 2-6: the spent medium was replaced every other day.

On Day 5 or 6: MEF culture dishes were prepared.

On Day 7: transduced cells were plated on MEF culture dishes in fibroblast medium.

On Day 8: the medium was changed to iPSC medium.

For 100 mL of complete iPSC medium the following component were mixed:
KnockOut™ DMEM/F-12 78 mL
KnockOut™ Serum Replacement (KSR) 20 mL
MEM Non-Essential Amino Acids Solution, 10 mM 1 mL
GlutaMAX™-I 1 mL
β-mercaptoethanol, 55 mM 100 μL
Penicillin-Streptomycin (optional) 1 mL
bFGF (10 μg/mL)*40 μL On Day 9-28: the spent medium was replaced every day and the culture vessels were monitored for the emergence of iPSC colonies. When iPSC colonies are ready for transfer,
they were picked and transfered onto fresh MEF culture dishes for expansion.

iPSC colony picking

The day before picking iPSC colonies, gelatin-coated 12-well feeder plates were prepared. Before picking colonies, 1 ml hES medium containing 10 μm Y27632 (ROCK (rho-associated kinase inhibitor) to each well of the plate was added and incubated it in a 37° C. incubator. Then, the iPSC colonies were examined under a microscope in a hood and the colonies were marked on the bottom of the dish. One colony was cut into small pieces with a 200 μL pipette and the cut pieces were transferred to the 12-well feeder plates with a 200 μL pipettes. The plate containing the picked colonies was incubated in a 37° C. incubator for 24-48 hours. After the colonies attach the plates, the medium was replaced with fresh hES medium and had been changed every day.

Viral production

The human Δ133p53 isoforms (β and γ) are cloned in the pMSCV-hyg (Clontech Laboratories, sold as a part of the Cat No 634401) vector for viral production. Viral particles were produced following next procedure:

On Day 1: 1-2×10$^6$ HEK 293T cells were plated into 100 mm plate dishes (growth medium: MEM supplemented with 10% FCS, sodium pyruvate, glutamine and antibiotics)

On Day 2: the first transfection was performed as follow:
Mixing in Tube 1
1 μg of vector containing viral gag/pol genes
1 μg of vector containing viral env gene
3 μg of pMSCV-hyg containing Δ133p53 isoform
250 μl of 150 mM NaCl
Mixing in Tube 2
250 μl of 150 mM NaCl
15 μl of JetPei transfection reagent (Polyplus Cat No 101-40)
Tube 1 and 2 were mixed.

The mixture was incubated 30 min at room temperature. In meantime the cells were washed and plated in 5 ml of growth medium without antibiotics.

After incubation, the mixture of Tubes 1 and 2 was added in drop wise manner to the cells and leaved for 4 hours. The cells were washed with PBS and 10 ml of growth medium with antibiotics was added.

If viral production requires more than one 100 mm dish with HEK 293T cells, the quantities of mixture in Tubes 1 and 2 have to be increased according to the number of the plates.

On Day 3: the second transfection was performed (same as for day 2)

On Day 5: the supernatant of transfected cell were collected and filtered using 0.2 μm sterile filter. Supernatant aliquot could be used immediately or stored at −80° C.

For infection, viral aliquots was slowly defrosted and added to target cells in the presence of polybrene (Hexadimethrine bromide, stock 10 mg/ml=1000×).

Example 1: Δ133p53β is Highly Expressed in ES and iPSC Compared to Dedifferentiated Cells The experimental protocol described above was used herein. Furthermore, 4 transcriptional factors (Oct4, Sox2, Klf4, c-myc) or 6 transcriptional factors (Nanog and Lyn28 in addition of the 4 factors) were added.

To analyze how human pluripotent stem cells adapt p53 alternative splicing during induction, maintenance and differentiation, Δ133p53β mRNA levels were analyzed by qPCR in iPSCs induced from fibroblasts with 4 factors (Oct4, Sox2, Klf4, c-myc) or 6 factors (Nanog and Lyn28 in addition of the 4 factors) after 3 weeks of reprogramming.

Generally, forced expression of the 4 factors Oct4, Sox2, Klf4 and c-myc is necessary and sufficient to generate iPSCs from non-senescent cells. However, it is already known that senescent and centenarian-derived pluripotent stem cells redifferentiate into fully rejuvenated cells only when Nanog and Lyn 28 are added to the four-factor combination (Lapasset et al; 2011).

Figure 2:
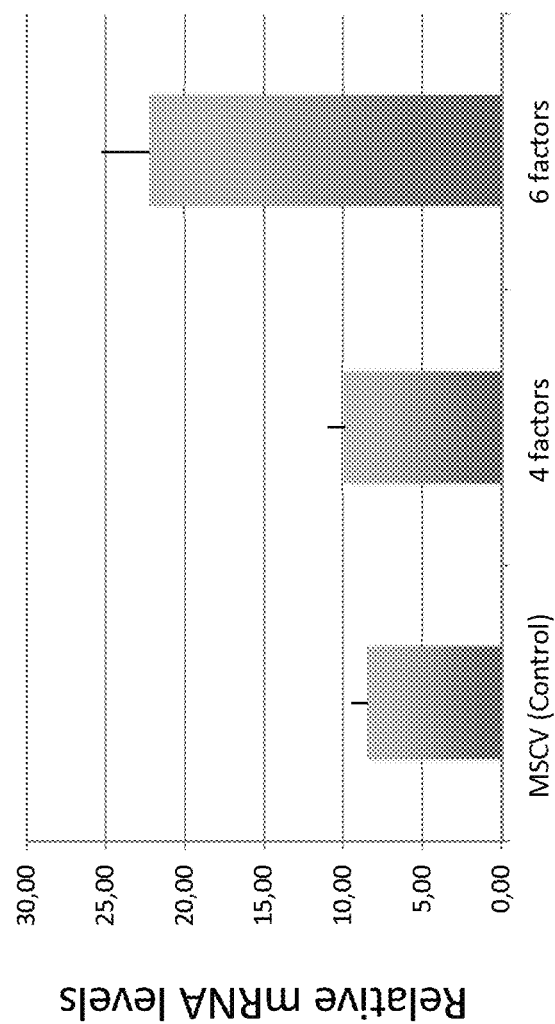
FIG. 2: Level of expression of Δ133p53β versus TBP in cells infected with 4 factors (Oct4, Sox2, Klf4, c-myc) and 6 factors (Oct4, Sox2, Klf4, c-myc, Nanog and Lyn28) after three weeks. Δ133p53β is highly expressed in human cells expressing the 6 Factors OSKMNL compared to 4 factors OSKM

The results as shown on FIG. 2 show that iPSCs induced from senescent fibroblasts with the 6-factor cocktail have higher levels of Δ133p53β than non-senescent cells induced with the 4 factors cocktail. This indicates that Δ133p53β might be involved in the reprogramming/reversion of senescent/aged cells for rejuvenation.

Figure 3:
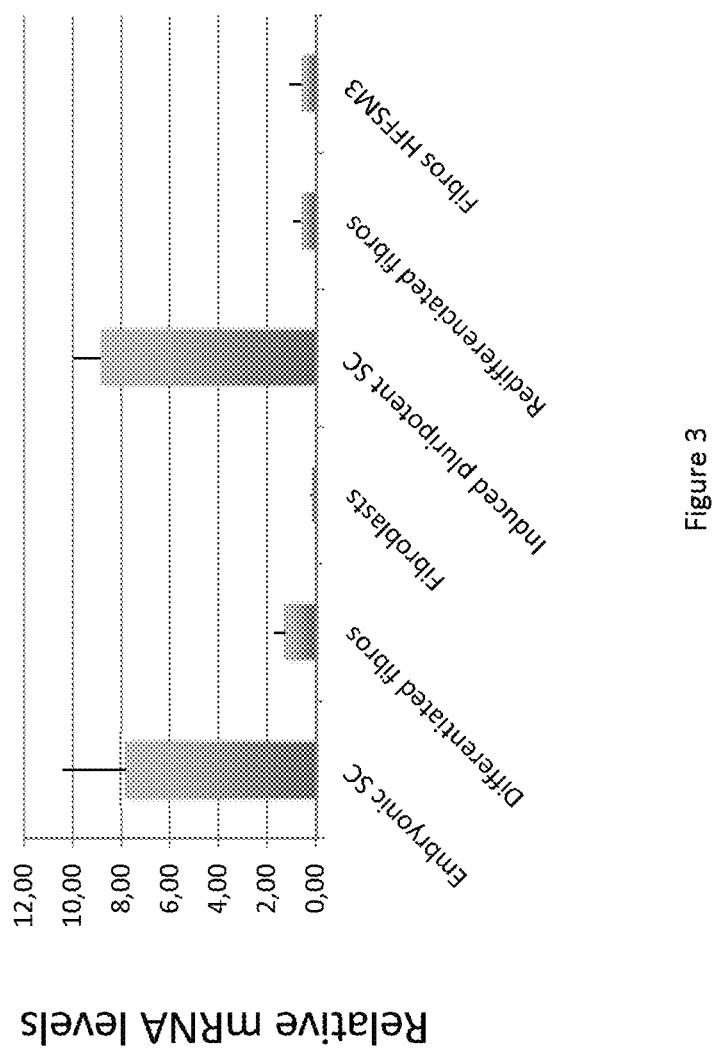
FIG. 3: Δ133p53β isoform expression in fibroblasts and stem cells. Δ133p53β is highly expressed in human embryonic stem cells and in iPSCs. Δ133p53β mRNA levels were analyzed by qPCR in human embryonic stem cells before (ES) and after (ES-F) fibroblastic differentiation, in skin fibroblasts before (Sk-F) and after (iPSCs) reprogramming and after re-differentiation (iPSC-F) and from human neonatal (HFFSM3). Δ133p53β is clearly increased in embryonic stem cells and in iPSCs compared to fibroblasts.

Δ133p53β_mRNA levels were also analyzed in human embryonic stem cells before (ES) and after (ES-F) fibroblastic differentiation, in skin fibroblasts before (Sk-F) and after (iPSCs) reprogramming and after re-differentiation (iPSC-F) and from human neonatal (HFFSM3). As shown on FIG. 3, mRNA expression of Δ133p53β is clearly increased in embryonic stem cells and in iPSCs compared to fibroblasts, indicating that elevated level of this isoform is not associated with genetic instability. This would provide a major advantage compared to mutant p53, which use in iPSC technology is hampered by genetic instability they confer.

Example 2: Δ133p53β Reprograms Fibroblasts into iPSC

Figure 4:
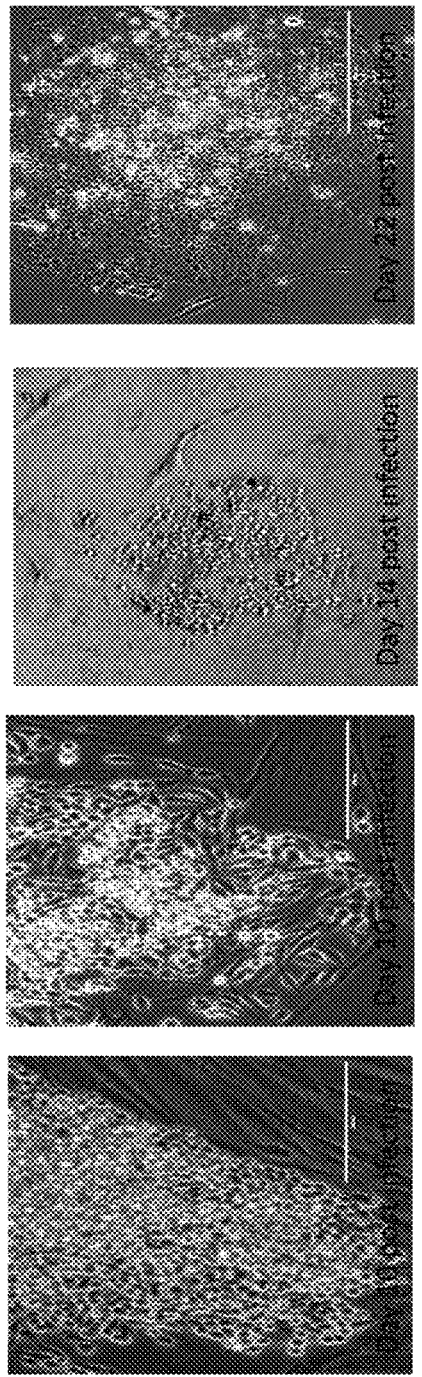
FIG. 4: Images of iPSC-like cells, produced only with the expression of Δ133p53β 10, 14 and 22 days post infection as indicated
Figure 5:
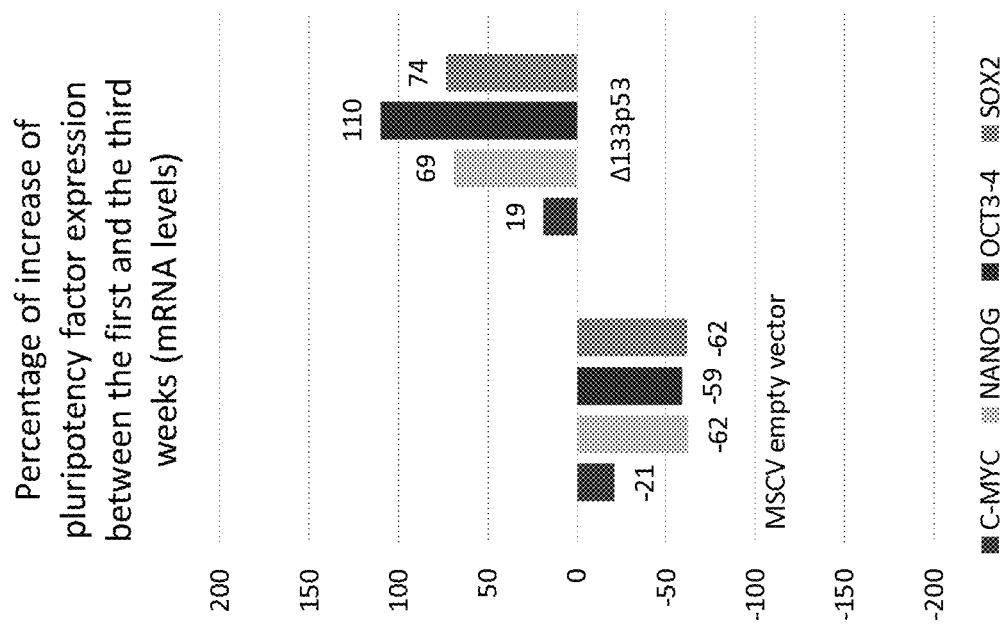
FIG. 5: Influence of Δ133p53β isoform on the expression of the pluripotency factors. Expression of Δ133p53β elicits an increase in Sox2, Nanog, Oct 3/4 and to a lesser extent c-myc mRNA levels between the first and the third weeks after reprogramming.

Human primary fibroblast cells were established from normal human foreskin and display a maximum of 72 population doublings before the onset of senescence. As shown on FIG. 5, Δ133p53β splice isoform of p53 produces iPSC-like cells, which express key regulators of pluripotency (FIG. 4).

Thus, it was chary demonstrated that herein used fibroblas are untransformed normal primary fibroblast.

Example 3: The Expression of Δ133p53β Isoform Preserves the Ability of Cells to Repair DNA p53 is a limiting factor in iPSC reprogrammation from normal cells and it is also considered that the alteration of p53 expression during the reprograming somatic cells to iPSC could lead to the formation of iPSC containing DNA damage and/or chromosomal abnormalities. To ascertain the expression of Δ133p53 isoforms do not affect the DNA damage and DNA repair response, the inventors have tested the transactivational function of p53 in normal fibroblasts expressing Δ133p53α isoform or Δ133p53β isoform in the presence of DNA breaks caused by a radiomimetic agent (bleomycin). Previous studies conducted by the inventors showed that normal fibroblasts stop their cell cycle in the presence of DNA breaks via the accumulation of p21WAF-1, which is an inhibitor of cyclin dependent kinases, (Baus et al, EMBO J. 2003; Gire et al, EMBO J. 2004, Jullien et al, NAR 2013).

Figure 6A:
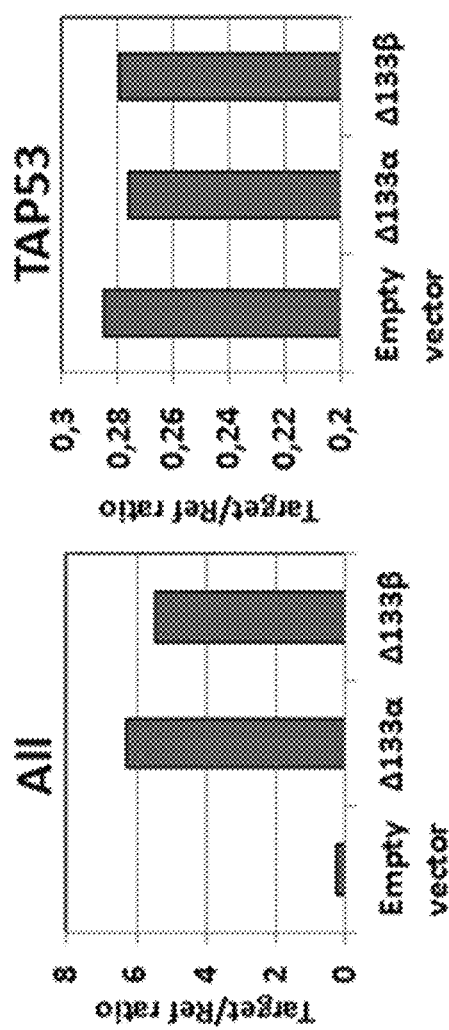
FIG. 6: Human skin fibroblasts expressing either empty vector (Empty vector) or Δ133p53α isoform (Δ133α) or Δ133p53β isoform (Δ133β). A: mRNA expression of p53 isoforms (Δ133p53α and Δ133p53β) measured by qPCR with specific primers to detect all isoforms (ALL) and primers to detect all isoforms except Δ133 (TAP53). qPCR results are expressed as target gene/reference gene ratio (TBP, TATA binding protein). B: mRNA expression of p21 and MDM2 measured by qPCR. C: Western blot showing the expression levels of the canonical p53α isoforms detected with antibody CM1, and Δ133p53α Δ133p53β isoforms detected with DO-11, γH2AX, phosphorylated Chk2 on Thr68 (P-Thr68-Chk2), Chk2 total proteins of the DNA damaged response pathway and p21, cell cycle inhibitors protein and pRb. γTubuline (γTub) is used as loading control.

Normal fibroblasts transduced by a construct encoding Δ133p53α or Δ133p53β or by an empty vector (pMSCV) were treated with bleomycin (10 µg/ml) for 6 hours and then the cells were collected. By quantitative PCR (q-PCR) the overexpression of Δ133p53α or Δ133p53β isoform mRNA in human fibroblasts have been respectively validated (FIG. 6A-AII). In addition it was shown that the overexpression of Δ133p53α or Δ133p53β isoform does not alter the mRNA expression of the other p53 isoforms (FIG. 6A-TAP53).

Figure 6B:
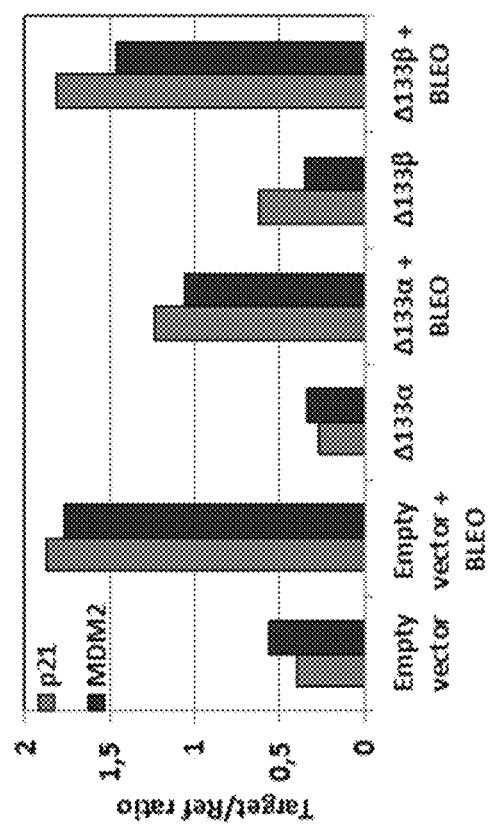
Figure 6C:
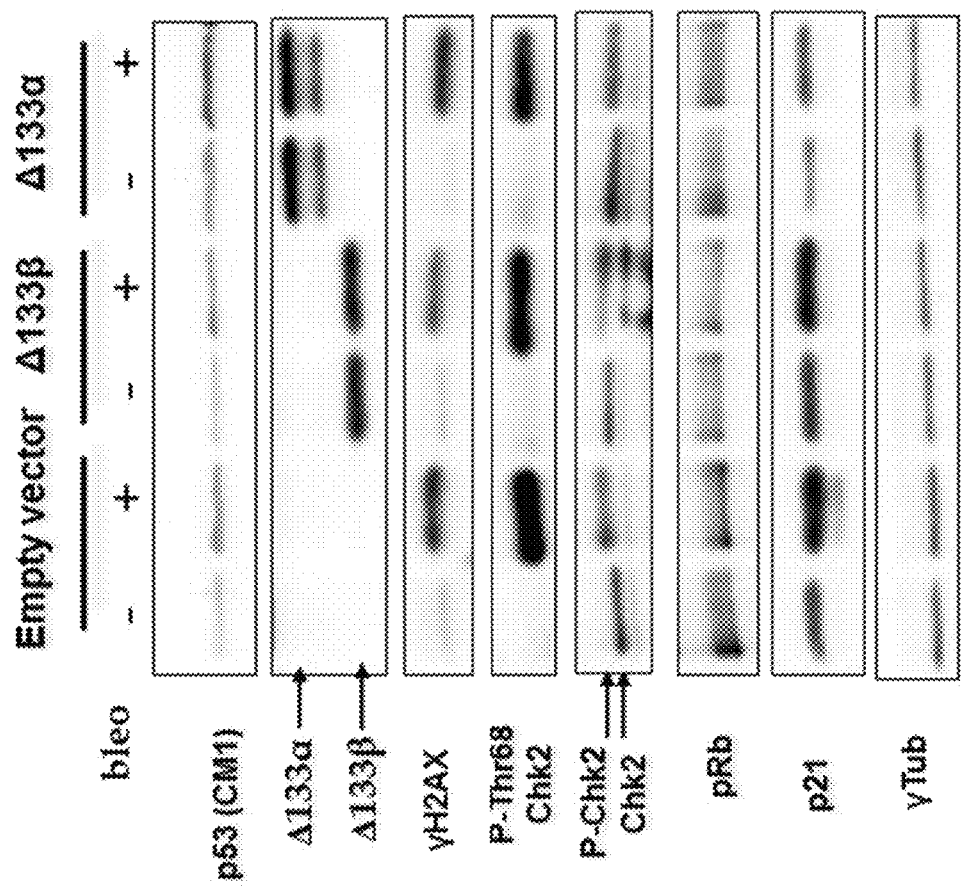

Analysis by q-PCR and Western blotting of the expression of p53 targets p21WAF-1 (inhibitors of cyclin/Cdks complex) and Mdm2 (proteins involved in p53 degradation) in cells expressing Δ133p53β shows that expressions of p21WAF-1 and Mdm2 are very comparable to those of the cells transduced by the control empty vector in the absence or presence of bleomycin (FIG. 6B, 6C). On the contrary, the overexpression of Δ133p53α leads to a significant reduction of mRNA and protein levels of p21WAF-1 accumulated in the cells (FIG. 6B, 6C). The expression of Δ133p53α thus prevents the accumulation of p21WAF1 in the presence of DNA damage, indicating that the transcriptional function of wild type p53 is altered in these cells. Histone variant H2AX and Chk2 kinase proteins, two proteins involved in the repair of DNA damages upstream of p53, are activated in cells expressing Δ133p53β and Δ133p53α.

The above data show that the transactivating function of p53 protein in response to DNA damage remains intact in normal fibroblasts expressing Δ133p53β isoform, whereas the same function of p53 is altered in cells expressing Δ133p53α isoform. This suggests that in case of DNA damage during reprogramming induced by Δ133p53β isoform, damaged cells (which retained an unaltered DNA repair machinery) will be able to exit the cell cycle (via the accumulation of p21 cell cycle inhibitor) and thus to be removed from the proliferative pool. The obtained final pool of reprogrammed iPSC cells should thus be free of cells with DNA damage or with altered DNA repair machinery.

BIBLIOGRAPHIC REFERENCES

Aoubala M, Murray-Zmijewski F, Khoury M P, Fernandes K, Perrier S, Bernard H, Prats A C, Lane D P, Bourdon J C, "p53 directly transactivates Δ133p53α, regulating cell fate outcome in response to DNA damage", Cell Death Differ. 2011 February; 18(2):248-58. doi: 10.1038/cdd.2010.91

Baus F., Gire V., Piette J., and Dulic V. 2003. Permanent cell cycle exit in G2 phase after DNA damage in normal human fibroblasts. EMBO J 22: 3992-4002.

Bourdon, J. C., Fernandes, K., Murray-Zmijewski, F., Liu, G., Diot, A., Xirodimas, D. P., Saville, M. K., and Lane, D. P. (2005). p53 isoforms can regulate p53 transcriptional activity. Genes a development 19, 2122-2137.

Bourdon, J. C. (2007). p53 and its isoforms in cancer. Br J Cancer 97, 277-282.

Gire V, Roux P., Wynford-Thomas D, Roux P., Brondello J.-M., and Dulic V. 2004. DNA damage checkpoint kinase Chk2 triggers replicative senescence. EMBO J 23:2554-63

Golebiewska A, Brons N H, Bjerkvig R, Niclou S P. Critical appraisal of the side population assay in stem cell and cancer stem cell research. Cell Stem Cell. 2011 Feb. 4; 8(2):136-47.

Hofstetter, G., Berger, A., Berger, R., Zoric, A., Braicu, E. I., Reimer, D., Fiegl, H., Marth, C., Zeimet, A. G., Ulmer, H., et al. (2012). The N-terminally truncated p53 isoform Delta40p53 influences prognosis in mucinous ovarian cancer. International journal of gynecological cancer: official journal of the International Gynecological Cancer Society 22, 372-379.

Hong, H., Takahashi, K., Ichisaka, T., Aoi, T., Kanagawa, O., Nakagawa, M., Okita, K., and Yamanaka, S. (2009). Suppression of induced pluripotent stem cell generation by the p53-p21 pathway. Nature 460, 1132-1135.

Jullien L., Mestre M, Roux P and Gire V. 2013. Eroded human telomeres are more prone to remain uncapped and to trigger a G2 checkpoint response. Nucleic Acids Research 41, 900-11.

Kawamura, T., Suzuki, J., Wang, Y. V., Menendez, S., Morera, L. B., Raya, A., Wahl, G. M., and Izpisua Belmonte, J. C. (2009). Linking the p53 tumour suppressor pathway to somatic cell reprogramming. Nature 460, 1140-1144.

Lapasset L, Milhavet O, Prieur A, Besnard E, Babied A, Aït-Hamou N, Leschik J, Pellestor F, Ramirez J M, De Vos J, Lehmann S, Lemaitre J M., "Rejuvenating senescent and centenarian human cells by reprogramming through the pluripotent state.", Genes Dev. 2011 Nov. 1; 25(21):2248-53.

Li, M., He, Y., Dubois, W., Wu, X., Shi, J., and Huang, J. (2012). Distinct regulatory mechanisms and functions for p53-activated and p53-repressed DNA damage response genes in embryonic stem cells. Mol Cell 46, 30-42.

Lin T1, Chao C, Saito S, Mazur S J, Murphy M E, Appella E, Xu Y., "p53 induces differentiation of mouse embryonic stem cells by suppressing Nanog expression", Nat Cell Biol. 2005 February; 7(2):165-71.

Lin, Y. and Chen, G., Embryoid body formation from human pluripotent stem cells in chemically defined E8 media (Jun. 1, 2014), StemBook, ed. The Stem Cell Research Community, StemBook.

Marcel et al, 2010 "Δ160p53 is a novel N-terminal p53 isoform encoded by Δ133p53 transcript".

Takenaka C, Nishishita N, Takada N, Jakat L M, Kawamata S, "Effective generation of iPS from CD34+ cord blood cells by inhibition of p53"; Experimental Hematology 2010, 38: 154-162.

Tapia N, Schöler H R., "p53 connects tumorigenesis and reprogramming to pluripotency", J Exp Med. 2010 Sep. 27; 207(10):2045-8. doi: 10.1084/jem.20101866.

Telford W G. Stem cell side population analysis and sorting using DyeCycle violet. Curr Protoc Cytom. 2010 January; Chapter 9:Unit9.30.

Terrier O, Marcel V, Cartet G, Lane D P, Lina B, Rosa-Calatrava M, Bourdon J C., Influenza A viruses control expression of proviral human p53 isoforms p53β and Delta133p53α, J Virol. 2012 August; 86(16):8452-60. 10.1128/JVI.07143-11.

WO2011/000891.

WO2012/044979

The invention claimed is:

1. An in vitro method for producing mammalian induced pluripotent stem cells (iPSCs), comprising:
   a) transducing isolated mammalian somatic cells with:
      i) at least one vector encoding a Δ133p53β isoform, Δ133p53γ isoform, or both Δ133p53β and Δ133p53γ isoforms, and
      ii) vectors encoding reprogramming factors Oct4, Sox2, Klf4, and cMyc;
   b) culturing the cells obtained in step a) in a medium supporting pluripotent cell expansion; and
   c) isolating iPSCs from the culture in step b).

2. The in vitro method according to claim 1, wherein the mammalian somatic differentiated cells comprise peripheral blood mononuclear cells (PBMC), fibroblasts or CD4+ lymphocytes.

3. The method of claim 1, wherein the at least one vector encoding a Δ133p53β isoform, Δ133p53γ isoform, or both Δ133p53β and Δ133p53γ isoforms is a retroviral vector and comprises elements necessary to allow expression thereof selected from a promoter, an enhancer or a regulatory sequence.

4. The in vitro method according to claim 1, wherein the medium of step b) is a basal medium comprising inorganic salts, amino acids, vitamins and glucose, β-mercaptoethanol, at least one antibiotic, and bFGF.

5. The in vitro method according to claim 1, wherein the induced pluripotent stem cells (iPSC) are isolated by a selection based on stem cells surface markers, an embryoid formation or iPSC colony picking.

6. The in vitro method according to claim 1, further comprising step a1) of culturing the mammalian somatic differentiated cells before the step a) of transducing said cells.

7. The in vitro method according to claim 1, wherein the mammalian somatic differentiated cells are transduced with vector expressing Δ133p53β isoform.

8. The in vitro method according to claim 1, wherein the mammalian somatic differentiated cells are fibroblasts.

9. The method of claim 1, wherein the at least one vector encoding a Δ133p53β isoform, Δ133p53γ isoform, or both Δ133p53β and Δ133p53γ isoforms is a murine stem cell viral (MSCV) vector and comprises elements necessary to allow expression thereof selected from a promoter, an enhancer or a regulatory sequence.

10. The in vitro method according to claim 1, said method further comprising step a1) of culturing the mammalian somatic differentiated cells before the step a) in which said cells are transduced with vector expressing Δ133p53β isoform.

11. The in vitro method according to claim 10, wherein the mammalian somatic differentiated cells are fibroblasts.

12. The in vitro method according to claim 11, wherein said fibroblasts are transduced with retroviral vector expressing Δ133p53β isoform.

13. The in vitro method according to claim 1, wherein the induced pluripotent stem cells (iPSC) are isolated by iPSC colony picking.

* * * * *

UNITED STATES PATENT AND TRADEMARK OFFICE
CERTIFICATE OF CORRECTION

| | | |
|---|---|---|
| PATENT NO. | : 10,767,165 B2 | |
| APPLICATION NO. | : 15/547212 | |
| DATED | : September 8, 2020 | |
| INVENTOR(S) | : Roux et al. | |

It is certified that error appears in the above-identified patent and that said Letters Patent is hereby corrected as shown below:

On the Title Page

Item (12) "Roux" is corrected to read --Roux et al.--.

Item (72) Inventor is corrected to read:
--Pierre Roux, Saint Gely-du Fesc (FR);
Nikola Arsic, Montpellier, (FR);
Gilles Gadea, Montpellier (FR);
Philippe Fort, Champagnier (FR);
Peggy Raynaud, Montpellier (FR)--.

Signed and Sealed this
Fourteenth Day of June, 2022

Katherine Kelly Vidal
*Director of the United States Patent and Trademark Office*